United States Patent
Raud et al.

(10) Patent No.: US 9,492,454 B2
(45) Date of Patent: *Nov. 15, 2016

(54) USE OF PEMIROLAST IN THE TREATMENT OF ACUTE ASTHMA

(71) Applicant: RSPR PHARMA AB, Stockholm (SE)

(72) Inventors: Johan Raud, Stockholm (SE); Carl-Johan Dalsgaard, Stockholm (SE); Jesper Säfholm, Stockholm (SE)

(73) Assignee: RSPR Pharma AB, Stockholm (SE)

( * ) Notice: Subject to any disclaimer, the term of this patent is extended or adjusted under 35 U.S.C. 154(b) by 0 days.

This patent is subject to a terminal disclaimer.

(21) Appl. No.: 15/016,012

(22) Filed: Feb. 4, 2016

(65) Prior Publication Data

US 2016/0175311 A1 Jun. 23, 2016

Related U.S. Application Data

(63) Continuation of application No. 14/909,221, filed as application No. PCT/GB2015/053190 on Oct. 23, 2015.

(60) Provisional application No. 62/067,759, filed on Oct. 23, 2014.

(51) Int. Cl.
*A61K 31/519* (2006.01)

(52) U.S. Cl.
CPC .......... *A61K 31/519* (2013.01); *Y10S 514/826* (2013.01)

(58) Field of Classification Search
None
See application file for complete search history.

(56) References Cited

U.S. PATENT DOCUMENTS 4,122,274 A 10/1978 Juby

FOREIGN PATENT DOCUMENTS

| EP | 0316174 A1 | 5/1989 |
|---|---|---|
| EP | 1285921 A1 | 2/2003 |
| WO | 2010146348 A2 | 12/2010 |

OTHER PUBLICATIONS

"Guidance for Industry: Estimating the Maximum Safe Starting Dose in Initial Clinical Trials for Therapeutics in Adult Healthy Volunteers", US FDA, Center for Drug Evaluation and Research, Jul. 2005, pp. 1-27.*
Kemp et al., "Pemirolast, A New Oral Nonbrochodilator Drug for Chronic Asthma," Annals of Allergy 68(6):488-91 (1992).
Yanagihara et al., "Immunopharmacological Studies on TBX, a New Antiallergic Drug (3) Inhibitory Effects on Histamine Release from Lung Fragments and Bronchoconstriction in Guinea Pigs," Japan J. Pharmacol. 51(1):83-92 (1989).
Hasegawa et al., "Kinetic Interaction Between Theophylline and a Newly Developed Anti-allergic Drug, Pemirolast Potassium," European Journal of Clinical Pharmacology 46(1):55-58 (1994).
Brannan et al., "Evidence of Mast Cell Activation and Leukotriene Release After Mannitol Inhalation," Eur. Respir. J. 22:491-6 (2003).
Busse, W.W., "The Relationship of Airway Hyperresponsiveness and Airway Inflammation. Airway Hyperresponsiveness in Asthma: Its Measurement and Clinical Significance," Chest 138(2):4S-10S (2010).
Drugs of Today, 28(1):29-31 (1992).
Hardy et al., "The Bronchoconstrictor Effect of Inhaled Prostaglandin D2 in Normal and Asthmatic Men," The New England Journal of Medicine 311(4):209-13 (1984).
Kurosawa, M., "Anti-Allergic Drug Use in Japan—The Rationale and the Clinical Outcome," Clinical and Experimental Allergy 24:299-306 (1994).
Leuppi, J.D., "Bronchoprovocation Tests in Asthma: Direct Versus Indirect Challenges," Curr. Opin. Pulm. Med. 20:31-6 (2014).
Taniguchi et al., "Antigen-Induced Airway Hyperresponsiveness in Infantile Guinea Pigs," Arerugi 47(8):720-5 (1998) (English abstract only).
Yanagihara et al., "Immunopharmacological Studies on TBX, a New Antiallergic Drug (1) Inhibitory Effects on Passive Cutaneous Anaphylaxis in Rats and Guinea Pigs," Japan J. Pharmacol. 48:91-101 (1988).
International Search Report and Written Opinion corresponding to PCT/GB2015/053190, mailed Jan. 15, 2016.
Roquet et al., "Combined Antagonism of Leukotrienes and Histamine Produces Predominant Inhibition of Allergen-Induced Early and Late Phase Airway Obstruction in Asthmatics," Am. J. Respir. Crit. Care Med. 155:1856-63 (1997).
Beasley et al., "Effect of a Thromboxane Receptor Antagonist on PGD2- and Allergen-Induced Bronchoconstriction," J. Appl. Physiol. 66:1685-93 (1989).
Dognéet al., "Therapeutic Potential of Thromboxane Inhibitors in Asthma," Expert Opin. Investig. Drugs 11(2):275-81 (2002).
Mathéet al., "Bronchial Hyperreactivity to Prostaglandin F2α and Histamine in Patients with Asthma," British Medical Journal 1:193-96 (1973).
Knight et al., "Histamine-Induced Contraction of Human Isolated Bronchus is Enhanced by Endogenous Prostaglandin F2α and Activation of TP Receptors," Eur. J. Pharmacol. 319:261-67 (1997).
Armour et al., "Characterization of Contractile Prostanoid Receptors on Human Airway Smooth Muscle," Eur. J. Pharmacol. 165:215-22 (1989).
Ninomiya et al., "General Pharmacological Study of TBX," Japanese Pharmacology and Therapeutics 17(4):121-51 (1989).
Deshpande et al., "Bitter Taste Receptors on Airway Smooth Muscle Bronchodilate by Localized Calcium Signaling and Reverse Obstruction," Nature Medicine 16(11):1299-1305 (2010).
Pharmaceutical Interview Form (IF)—Alegysal (2007).
Yoshida et al., "Clinical Evaluation of an Oral Antiallergic Agent, TBX Tablet, in Adult Bronchial Asthma: A Multi-Center, Double-Blind Study in Comparison with Tranirast," Japanese Pharmacology & Therapeutics 17(3):1-61 (1989) (English translation only).
Taniguchi et al., "Antigen-Induced Airway Hyperresponsiveness in Infantile Guinea Pigs," Arerugi 47(8):720-5 (1998) (full article with English translation).

* cited by examiner

*Primary Examiner* — Savitha Rao
*Assistant Examiner* — Gregg Polansky
(74) *Attorney, Agent, or Firm* — LeClairRyan, a Professional Corporation

(57) ABSTRACT

According to the invention there is provided pemirolast, or a pharmaceutically acceptable salt thereof, for use in the therapeutic treatment of asthma, such as an acute asthma attack. Suitable lower doses of pemirolast are least about 110 mg per day.

8 Claims, 7 Drawing Sheets

USE OF PEMIROLAST IN THE TREATMENT OF ACUTE ASTHMA

This application is a continuation of U.S. application Ser. No. 14/909,221, which is a national stage application under 35 U.S.C. §371 of PCT Application No. PCT/GB2015/053190, filed Oct. 23, 2015, which claims the priority benefit of U.S. Provisional Patent Application Ser. No. 62/067,759, filed Oct. 23, 2014.

FIELD OF THE INVENTION

This invention relates to a new pharmaceutical use.

BACKGROUND AND PRIOR ART

Asthma is one of the most common chronic inflammatory diseases, known to affect nearly 25 million citizens in the US alone. In childhood, it is the most common chronic disease, affecting in the region of an estimated 7 million US children.

The pathophysiology of asthma is complex and involves airway inflammation, intermittent airflow obstruction, and bronchial hyper-responsiveness, resulting in shortness of breath, wheezing, coughing, chest tightness and/or pain, as well as other non-specific symptoms in young children, including recurrent bronchitis, bronchiolitis, or pneumonia and the like.

Diagnosis may be made under guidelines from the (US) National Asthma Education and Prevention Program and include prevalence of episodic symptoms of airflow obstruction and/or at least partially reversible airflow obstruction or symptoms, followed by spirometry with post-bronchodilator response, and/or chest radiography (mainly to rule out other pulmonary diseases), as more definitive diagnostic tools.

There is presently no cure for asthma, and treatments often revolve around avoidance of known triggers, such as allergens, dust, pollutants, etc.

In the management and/or treatment of asthma, the ultimate goal is to prevent symptoms, minimize morbidity and prevent functional and psychological morbidity to provide a healthy (or near healthy) lifestyle.

However, there is also a need to treat effectively acute asthma episodes. Such acute exacerbations of asthma are usually commonly referred to as "asthma attacks". Symptoms include shortness of breath, wheezing, and tightness in the chest. In severe cases, breathing may be significantly impaired such that the condition may become life-threatening.

Acute asthma attacks can often be brought on by infections, allergens, air pollution, exercise or insufficient or inappropriate medication use.

The most commonly-used active agents are presently employed to prevent asthma episodes ("preventers"). Such medications make the airways less sensitive, reduce airway inflammation and help to dry up mucus. Such preventers need to be taken every day to prevent symptoms and asthma attacks, and it may take a few weeks before they reach their full effect. Preventer medications include long-acting bronchodilators, oral theophylline, inhaled corticosteroids, leukotriene modifiers, cromones (cromolyn or nedocromil) and anti-IgE antibodies.

On the other hand, relief medications ("relievers") are fast acting medications that give quick relief of existing asthma symptoms or "attacks" (wheeze, cough, shortness of breath). They are bronchodilators, which means that they relax the muscle around the outside of the airway, which opens the airway. Every asthmatic patient should have a reliever medication. There are three main categories of reliever medication: theophylline; short-acting beta-agonists, such as terbutaline and salbutamol; and anticholinergics, such as ipratropium.

A more severe condition, known as status asthmaticus or acute severe asthma, is an acute exacerbation of asthma that does not respond well to such standard treatments.

Additionally, there are drawbacks associated with all of the aforementioned drugs (particularly inhaled corticosteroids), including lack of efficacy, non-adherence to treatment regimens, tolerance dependence and safety profiles/side-effects. Accordingly, there is thus a real clinical need for safer and/or more effective treatments of asthma.

Asthmatic bronchoconstriction in humans is mainly caused by mediators activating histamine 1 (H1) receptors (histamine), cysteinyl leukotriene 1 (CysLT1) receptors (leukotrienes C4-D4) and the prostanoid TP receptor (prostaglandin D2 (PGD2), prostaglandin F2α (PGF2α), thromboxane A2 (TXA2); see e.g. Roquet et al, *Amer. J. Resp. Crit. Care Med.* (1997) 155, 1856-1863 and Beasley et al, *J. Appl. Physiol.* (1989) 66, 1685-93).

The prostanoid TP receptor has gained much attention as a target for asthma drugs. The TP antagonist seratrodast is available for asthma treatment on the Japanese market (see e.g. Dogne et al, *Expert Opin. Investig. Drugs* (2002) 11, 275-81).

Asthmatics have been shown to be extremely sensitive to PGF2α when compared to healthy non-asthmatics. It has been suggested that endogenous, locally-formed PGF2α may play an important part in the pathogenesis of asthma (see Mathé et al, *Br. Med. J.* (1973) 1, 193-96). It is well established that PGF2α contracts human airways by stimulation of the TP receptor (Knight et al, *Eur. J. Pharmacol.* (1997) 319, 261-267 and Armour et al, *Eur. J. Pharmacol.* (1989) 165, 215-22).

Pemirolast is an orally-active anti-allergic mast cell inhibitor that is used in the prevention of conditions such as asthma, allergic rhinitis and conjunctivitis. See, for example, U.S. Pat. No. 4,122,274, European Patent Applications EP 316 174 and EP 1 285 921 and *Drugs of Today*, 28, 29 (1992). The drug is only known for the prophylaxis (i.e. preventative treatment) of asthma, and indeed has been marketed for over 20 years for such use in e.g. Japan as the potassium salt in 5 and 10 mg doses (equating to 4.25 and 8.5 mg of the free acid, respectively) e.g. under the trademark ALEGYSAL™. Two doses are administered every day to provide an immediate mast cell stabilising effect and so the short-term prevention of asthma attacks resulting from subsequent challenge by the aforementioned asthma triggers.

In a paper published in 1989 by Yanagihara et al (see *Japan J. Pharmacol.*, 51, 83 (1989)), studies were performed on pemirolast in an experimental bronchoconstriction model.

Although pre-administration with pemirolast inhibited antigen- and PAF-induced bronchoconstriction in guinea pigs in vivo, pre-treatment of isolated tracheal muscle from guinea pigs with pemirolast at concentrations of 10 μg/mL was found to have no effect on bronchoconstriction (i.e. pre-administration gave rise to no direct bronchodilatory effect on smooth tracheal muscle) when the latter was induced by either leukotriene $D_4$ or $PGF_{2\alpha}$.

Although much higher concentrations did give rise to some effect, 10 μg/mL equates to a single dose of about 125 mg, which is almost 15 times the clinical dose that is employed in the prophylaxis of asthma.

More significantly, a paper by Ninomiya et al in *Japanese Journal of Pharmacology and Therapeutics,* 17, 121 (1989) investigated the effect of pemirolast on isolated guinea pig trachea pre-constricted with acetylcholine, histamine, serotonin and barium chloride at higher doses than those presently employed in the clinic. These authors observed potencies of one seventh of that of the well-known, and at that time widely-used, bronchodilator, theophylline, and concluded that the results were not clinically significant.

Accordingly, the conclusion of these studies, and in the art generally (confirmed by Kemp et al in a paper entitled: "*Pemirolast, a new oral nonbronchodilator drug for chronic asthma*" in Annals of Allergy, 68, 488 (1992) who used twice daily 50 mg doses in humans), is that, when used clinically, pemirolast has no direct bronchodilator activity.

We have found surprisingly that pemirolast is capable of acting as a bronchodilator in human lung tissue, that is, reversing pre-induced bronchoconstriction at concentrations of about 10 μg/mL or higher. We have also found that pemirolast has a previously-undisclosed and unappreciated plasma concentration (exposure) profile which means that it can be employed in doses that are significantly higher than those presently employed in the prevention of asthma, and which are not only safe, but give rise to exposure levels in humans that correspond to those plasma concentrations at which pemirolast appears to be capable of acting, unexpectedly, as a bronchodilator in human patients. Accordingly, at such high doses, pemirolast is potentially of use in the therapeutic treatment of asthma, and in particular in the treatment of acute asthma episodes.

DISCLOSURE OF THE INVENTION

According to the invention, there is provided pemirolast, or a pharmaceutically acceptable salt thereof, for use in the therapeutic treatment of asthma, particularly the therapeutic treatment of acute asthma.

The term "acute asthma" will be understood to include any episode in an asthmatic patient (whether formally diagnosed or otherwise), where there is an apparent or measurable decrease in airflow and/or exacerbations of asthmatic symptoms, including wheezing, coughing, difficulty in breathing, etc. Acute asthma may be characterized by peak expiratory flow (PEF) and/or spirometry (ratio of forced expiratory volume in one second (FEV1) to forced vital capacity (FVC)) that are reduced by $\geq 10\%$. The term thus includes the conditions variously known as acute asthmatic episodes, asthmatic bronchoconstriction, exercise-induced bronchoconstriction, asthma/asthmatic exacerbations, severe asthma, acute severe asthma, status asthmaticus, brittle asthma (including Type 1 and Type 2 brittle asthma).

According to a second aspect of the invention there is provided a method of therapeutic treatment of asthma, particularly the therapeutic treatment of acute asthma, which method comprises the administration of a pharmacologically-effective amount of pemirolast, or a pharmaceutically acceptable salt thereof, to a patient in need of such treatment.

For the avoidance of doubt, in the context of the present invention, the term "therapeutic treatment" includes the therapeutic, or palliative, treatment of symptoms in patients having, or showing signs of, asthma, particularly acute asthma and/or asthma attacks, or any other relevant condition mentioned herein.

"Patients" include mammalian (particularly human) patients.

As described hereinafter, we have found that pemirolast is capable at certain high doses of selectively (compared to other agonists) reversing bronchoconstriction previously induced in human tissue by the thromboxane $A_2$ ($TXA_2$) receptor agonists, $PGF_{2\alpha}$ and U-46619 (a stable analog of the endoperoxide prostaglandin H2 and exhibits properties similar to $TXA_2$).

For the reasons discussed above, it is believed that this renders pemirolast and salts thereof of potential utility in the clinical therapeutic treatment of asthma, such as acute asthma and related conditions, and also, contrary to what is stated in the literature, as a bronchodilator, particularly in humans.

Accordingly, there is further provided the clinical therapeutic use of pemirolast, or a pharmaceutically acceptable salt thereof, as a bronchodilator.

Pharmaceutically-acceptable salts of pemirolast that may be mentioned include acid addition salts and base addition salts. Such salts may be formed by conventional means, for example by reaction of a free acid or a free base form of an active ingredient with one or more equivalents of an appropriate acid or base, optionally in a solvent, or in a medium in which the salt is insoluble, followed by removal of said solvent, or said medium, using standard techniques (e.g. in vacuo, by freeze-drying or by filtration). Salts may also be prepared by exchanging a counter-ion of an active ingredient in the form of a salt with another counter-ion, for example using a suitable ion exchange resin.

Preferred salts of pemirolast include alkaline earth, and more particularly alkali, metal salts, such as calcium, magnesium, preferably potassium salts (e.g. pemirolast potassium) and sodium salts (e.g. pemirolast sodium hemihydrate, as described in international patent application WO 2010/146348).

In the uses and methods described herein, pemirolast and salts thereof are preferably administered locally or systemically, for example orally, intravenously or intraarterially (including by intravascular or other perivascular devices/dosage forms (e.g. stents)), intramuscularly, cutaneously, subcutaneously, transmucosally (e.g. sublingually or buccally), rectally, transdermally, nasally, pulmonarily (e.g. tracheally, bronchially or by inhalation), topically, or by any other parenteral route, in the form of a pharmaceutical preparation comprising the compound in a pharmaceutically acceptable dosage form. Preferred modes of delivery include oral, intravenous, cutaneous or subcutaneous, nasal, intramuscular, or intraperitoneal delivery.

Pemirolast and salts thereof will generally be administered in the form of one or more pharmaceutical formulations in admixture with a pharmaceutically acceptable adjuvant, diluent or carrier, which may be selected with due regard to the intended route of administration and standard pharmaceutical practice. Such pharmaceutically acceptable carriers may be chemically inert to the active compounds and may have no detrimental side effects or toxicity under the conditions of use. Such pharmaceutically acceptable carriers may also impart an immediate, or a modified, release of pemirolast/salt thereof.

Suitable pharmaceutical formulations may be commercially available or otherwise are described in the literature, for example, Remington *The Science and Practice of Pharmacy,* 19th ed., Mack Printing Company, Easton, Pa. (1995) and *Martindale—The Complete Drug Reference* (35th Edition) and the documents referred to therein, the relevant disclosures in all of which documents are hereby incorporated by reference. Otherwise, the preparation of suitable formulations may be achieved non-inventively by the skilled person using routine techniques.

Administration of pemirolast or salt thereof may be continuous or intermittent (e.g. by bolus injection). The mode of administration may also be determined by the timing and frequency of administration, but is also dependent, in the case of the therapeutic treatment of asthma, on the severity of the condition. For example in the case of a mild to moderate asthma attack (e.g. exercise-induced asthma), pemirolast may be administered perorally. In case of more severe asthma attacks, pemirolast may be administered by inhalation and in the case of a severe asthma attack, in which, for example, a patient may be hospitalized, a bolus injection may be administered.

Similarly, the amount of pemirolast or salt thereof in the formulation will depend on the severity of the condition, and on the patient, to be treated, but may be determined by the skilled person.

However, as described hereinafter, we have found that pemirolast may be administered to humans at doses that are significantly higher than those presently employed in humans in the prevention of asthma, which doses are not only safe, but also give rise to plasma concentrations that allow it to treat asthma in a different manner, i.e. therapeutically, e.g. as a bronchodilator. Accordingly, suitable lower daily doses (calculated as the free acid), irrespective of the route of administration, in adult patients (average weight e.g. 70 kg), may be about 110 mg, such as about 120 mg, for example about 125 mg, per day. Preferred lower daily doses (calculated as the free acid), irrespective of the route of administration, may be about 200 mg, such as about 300 mg, for example about 350 mg, including about 400 mg, per day. Doses may be split into two or more individual doses per day.

According to a further aspect of the invention there is provided pemirolast, or a pharmaceutically acceptable salt thereof, for use in the (e.g. clinical) treatment of asthma, particularly the therapeutic (e.g. clinical) treatment of asthma, such as acute asthma, wherein pemirolast is administered at a dose of at least about 110 mg per day (calculated as the free acid). This corresponds to doses of about 1.5 mg/kg of body weight per day in all subjects irrespective of size or age.

In relation to this latter aspect of the invention, it is to be noted that the treatment of asthma is not limited to therapeutic treatment, but rather also encompasses the prophylactic treatment (by which we mean the prevention of an e.g. allergen-induced asthma attack), and/or diagnosis of patients which are susceptible to asthma, or other relevant conditions mentioned herein.

We have unexpectedly found that, at the aforementioned higher doses, pemirolast may be used in the prophylactic treatment of (e.g. allergen-induced) asthma attacks even when those doses of pemirolast are administered one day or more (e.g. up to two days, such as up to three days, or even one, two or three weeks) prior to exposure to the relevant antigen, when there was no pemirolast remaining in plasma to provide its known short-term/immediate biological effect as a mast cell stabiliser.

Subjects being administered placebo have been found to be less responsive to an attempted mannitol-induced asthma attack only after having been administered a high dose of pemirolast, several days previously.

This unexpected effect therefore appears to have nothing to do with pemirolast's understood mechanism of action as a mast cell stabiliser. For example, Yanagihara et al have reported (in *Japan J. Pharmacol.*, 48, 91 (1988)) that, after peroral administration of currently-employed clinical doses, pemirolast ceases to have a protective effect against IgE-induced passive cutaneous anaphylaxis (and therefore no mast cell stabilising/inhibitory effect) as little as 240 minutes (i.e. 4 hours) after administration.

Suitable upper limits of peroral daily dose ranges may be about 1,000 mg, such as about 800 mg, including about 600 mg, for example about 400 mg, such as about 300 mg. Suitable upper limits for inhalation may be about 200 mg. Suitable upper limits for injectable bolus administration (e.g. subcutaneous or intravenous administration) may be about 5 g, for example about 2 g, such as about 0.8 g per day. (All of the above doses are calculated as the free acid and, again, doses may be split into two or more individual doses per day.)

In any event, the medical practitioner, or other skilled person, will be able to determine routinely the actual dosage, which will be most suitable for an individual patient, depending on the severity of the condition and route of administration. The above-mentioned dosages are exemplary of the average case; there can, of course, be individual instances where higher or lower dosage ranges are merited, and such are within the scope of this invention.

For example, calculated as the free acid, suitable lower dose limits are about 1.5 mg/kg of body weight per day (calculated as the free acid), irrespective of the mode of administration. Again, calculated as the free acid, suitable upper limits of peroral daily dose ranges may be about 15 mg/kg of body weight, for inhalation may be up to about 3 mg/kg of body weight; and for injectable bolus administration may be up to about 75 mg/kg of body weight.

Peroral and inhaled doses may be given between once and four times daily, preferably three times daily and more preferably twice daily.

The dose administered to a mammal, particularly a human, in the context of the present invention should be sufficient to effect a response in the mammal (e.g. human) over a reasonable timeframe (as described hereinbefore). One skilled in the art will recognize that the selection of the exact dose and composition and the most appropriate delivery regimen will also be influenced by inter alia the pharmacological properties of the formulation, the nature and severity of the condition being treated, and the physical condition and mental acuity of the recipient, as well as the age, condition, body weight, sex and response of the patient to be treated, and the stage/severity of the disease, as well as genetic differences between patients.

In the uses and methods described herein, pemirolast and pharmaceutically acceptable salts thereof may also be combined with one or more active ingredients that are useful in the treatment of asthma. Such patients may thus also (and/or already) be receiving such asthma therapy based upon administration of one or more of such active ingredients, by which we mean receiving a prescribed dose of one or more of those active ingredients mentioned herein, prior to, in addition to, and/or following, treatment with pemirolast or salt thereof.

Pharmaceutically-acceptable salts, and doses, of other active ingredients useful in the therapeutic treatment of asthma include those that are known in the art and described for the drugs in question to in the medical literature, such as *Martindale—The Complete Drug Reference* (35$^{th}$ Edition) and the documents referred to therein, the relevant disclosures in all of which documents are hereby incorporated by reference.

Wherever the word "about" is employed herein, for example in the context of amounts (e.g. doses or concentrations of active ingredients), or time periods, it will be appreciated that such variables are approximate and as such may vary by ±10%, for example ±5% and preferably ±2% (e.g. ±1%) from the numbers specified herein.

The uses/methods described herein may have the advantage that, in the (e.g. therapeutic) treatment of asthma, such as acute asthma, they may be more convenient for the physician and/or patient than, be more efficacious than, be less toxic than, have a broader range of activity than, be more potent than, produce fewer side effects than, or that it may have other useful pharmacological properties over, similar methods (treatments) known in the prior art for use in such therapy.

The invention is illustrated, but in no way limited, by the following example, in which FIG. 1 shows mean plasma pemirolast concentrations (semi-log) versus time on Day 5 during a multiple-dose, open safety and tolerability study;

EXAMPLES

Example 1

Pharmacokinetics of Pemirolast in Humans

This study comprised 18 healthy male subjects, 18-45 years of age, and was a single and multiple-dose, open study assessing the safety and tolerability of pemirolast potassium tablets (10 mg, Ulgixal™ tablets) with the doses 10, 30 and 50 mg (containing 8.5, 25.5 and 42.5 mg pemirolast free acid, respectively) b.i.d. (6 subjects in each dose group).

The subjects received a single dose on the first day, then b.i.d. for three days and a single dose on the fifth day. The study was performed at the Berzelius Clinical Research Center AB in Linköping, Sweden. All laboratory pharmacokinetic analyses were performed by Quintiles AB, Uppsala, Sweden. Pharmacokinetic calculations were performed by Pharm Assist Sweden AB, Uppsala, Sweden.

Figure 1:
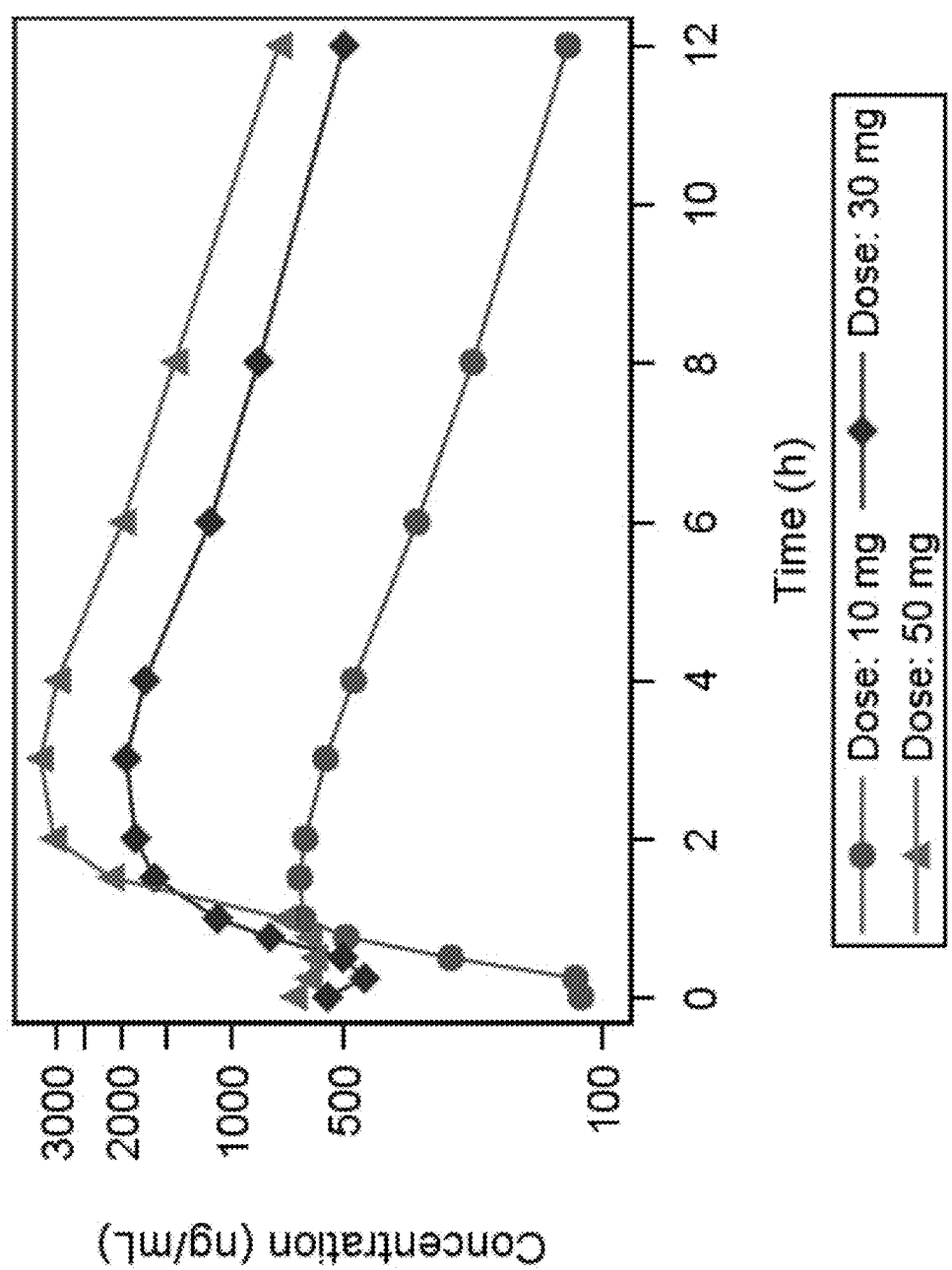

Mean $C_{max}$ data after multiple dosing are shown in and Table 1, and mean plasma concentrations over time on Day 5 are shown in FIG. 1.

TABLE 1

Multiple dose pharmacokinetics of orally administered pemirolast potassium; 10, 30 and 50 mg doses

|  |  | Dose | | |
|---|---|---|---|---|
|  |  | 10 mg (N = 6) | 30 mg (N = 6) | 50 mg (N = 6) |
| $C_{max}$ (μg/mL) | Mean | 0.73 | 2.04 | 3.42 |

Based on these clinical data, $C_{max}$ predictions were made (assumption: Linear pharmacokinetics when extrapolating to higher dose levels) and are presented in Table 2.

TABLE 2

$C_{max}$ Predictions

| Multiple dose | Exposure parameter | Value | Predicted values (mg) | | |
|---|---|---|---|---|---|
|  |  |  | 125 | 200 | 400 |
| 8.5 mg | $C_{max}$ (μg/mL) | 0.73 | 10.68 | 17.08 | 34.16 |
| 25.5 mg | $C_{max}$ (μg/mL) | 2.04 | 9.98 | 15.98 | 31.95 |
| 42.5 mg | $C_{max}$ (μg/mL) | 3.42 | 10.07 | 16.12 | 32.23 |

Thus, multiple oral b.i.d. dosing with 125 mg pemirolast is predicted to result in plasma concentrations ($C_{max}$) of about 10 μg/ml. To the applicant's knowledge pharmacokinetics of multiple b.i.d. doses of 25.5 mg pemirolast (30 mg pemirolast potassium) or higher have not previously been studied in man.

Later pharmacokinetic studies in healthy volunteers (7 to 8 in each group) have shown that actual $C_{max}$ values for various multiple doses (b.i.d. for three and a half days) are as follows:
80 mg-8.84 μg/mL
200 mg-32.55 μg/mL
320 mg-50.95 μg/mL.

Pemirolast was found to be safe and well-tolerated at all of these doses.

Example 2

Toxicokinetics of Pemirolast in the Dog

In a study in the Beagles, systemic pemirolast exposure was determined for orally administered pemirolast potassium at 75 mg/kg daily for 7 consecutive days in male and female dogs (75 mg/kg daily having been found to be a safe chronic dose in dogs). The study, including all analyses and calculations, were performed by WIL Research, France, in compliance with Good Laboratory Practices (GLP).

There were no major differences in kinetics between males and females. Mean $C_{max}$ is shown in Table 3.

TABLE 3

| | 75 mg/kg repeated dose (7th day) | |
|---|---|---|
| Variables | Males (n = 3) | Females (n = 3) |
| $C_{max}$ (μg/mL) | 168 | 150 |

Example 3

Effect of Pemirolast of hERG Channels

This study was performed by PhysioStim, France, a GLP compliant facility.

The effects of pemirolast on hERG currents in HEK-293 cells stably expressing the hERG potassium channel were studied using patch-clamp technique. In these experiments, 2.7, 8.0, 26.6 and 79.9 μg/mL of pemirolast potassium concentration-dependently decreased hERG tail current amplitude by 5.4%, 10.2%, 14.1% and 19.0%, respectively.

The reference compound E-4031 (0.1 μmol/L), a selective hERG inhibitor, reduced hERG tail current amplitude by 82.0%, thus confirming the pharmacological sensitivity of the hERG potassium channel in these experiments. In conclusion, $IC_{50}$ for pemirolast could not be calculated because the inhibition was less than 20% at the highest concentration tested.

These results show that pemirolast lacks potential to inhibit hERG channel (an important human "anti-target" that must be avoided during drug development to reduce the risk of certain potentially fatal cardiac adverse effects) at concentrations up to about 80 µg/mL.

Example 4

Bronchodilatory Effects of Pemirolast

Macroscopically healthy human lung tissue was obtained from patients undergoing lobectomy and placed immediately in ice-cold Krebs-Ringer PSS buffer.

Within 2 hours of the resection, bronchial tissue was, using microscopy, identified and gently dissected clear from lung parenchyma under ice-cold Krebs-Ringer PSS buffer condition, cut into intact rings (approximately 0.5-1 mm inner airway diameter and 3-4 mm in length) and placed in separate culture plate wells containing Dulbecco's modified Eagle medium under sterile conditions. The culture plate was placed in a humidified incubator (37° C. at 95% $O_2$ and 5% $CO_2$) for 17-24 hours.

On the day of the experiment, the bronchi were mounted horizontally between two metal prongs for recording of isometric tension using a myograph containing Krebs-Ringer PSS and kept at 37° C., constantly bubbled with carbogen (5% $CO_2$ in 95% $O_2$) to maintain pH at 7.4 (Organ Bath Model 700MO, DMT A/S, Aarhus, Denmark).

Preparations were allowed to equilibrate for 30 minutes with buffer changed every 15 minutes followed by a stepwise increase in tension over 60 minutes to a resting tension of 1.5 mN.

After the equilibration period, potassium chloride (60 mM) was added twice with a washout in between to ascertain bronchial reactivity and viability. This was followed by 60 minutes equilibration including several washes to allow the segment to return to baseline tension.

To investigate effects on bronchoconstriction, segments were contracted with different bronchoconstrictor mediators/agents prior to a cumulative addition of pemirolast potassium (10+100 µg/mL). Stock solutions of $PGF_{2\alpha}$, U-46619 and leukotriene $D_4$ were made in DMSO. Histamine, carbachol, KCl and pemirolast were dissolved in purified water. On the experimental day, further dilutions of pemirolast was performed in purified water whereas the other agonist were diluted in Krebs-Ringer PSS buffer.

Figure 2:
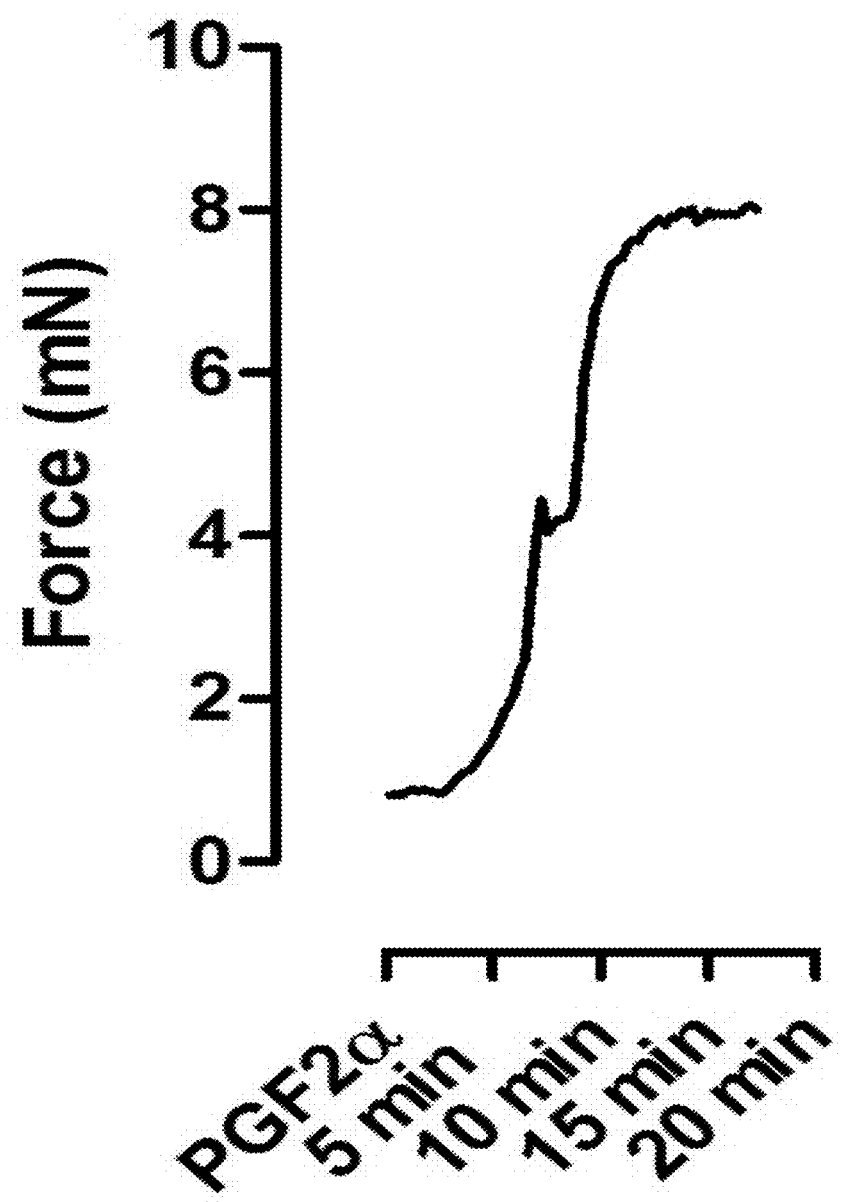
FIG. 2 shows PGF2α (3 μM) inducing a stable pre-contraction of approximately 70% of maximal contractibility.

$PGF_{2\alpha}$ (3 µM) induced a stable precontraction of approximately 70% of maximal contractibility as illustrated in FIG. 2. Addition of pemirolast (10 µg/ml, when the $PGF_{2\alpha}$ induced contraction had stabilised after 30-40 min) reversed the $PGF_{2\alpha}$-induced bronchoconstriction (force) by 21.5±4.4% within 15 min (n=4), and increasing the concentration of pemirolast to 110 µg/mL (by adding 100 µg/mL pemirolast 15 min after the addition of 10 µg/ml pemirolast) reduced the bronchoconstriction by 72.0±12.6% (n=4) within 40 min. The corresponding vehicle-treated segments relaxed 6.8±3.1% and 18.6±4.9%, respectively. Mean net changes (reductions) of $PGF_{2\alpha}$ induced bronchoconstriction (force) by pemirolast are shown in FIGS. 3 and 4.

Figure 3:
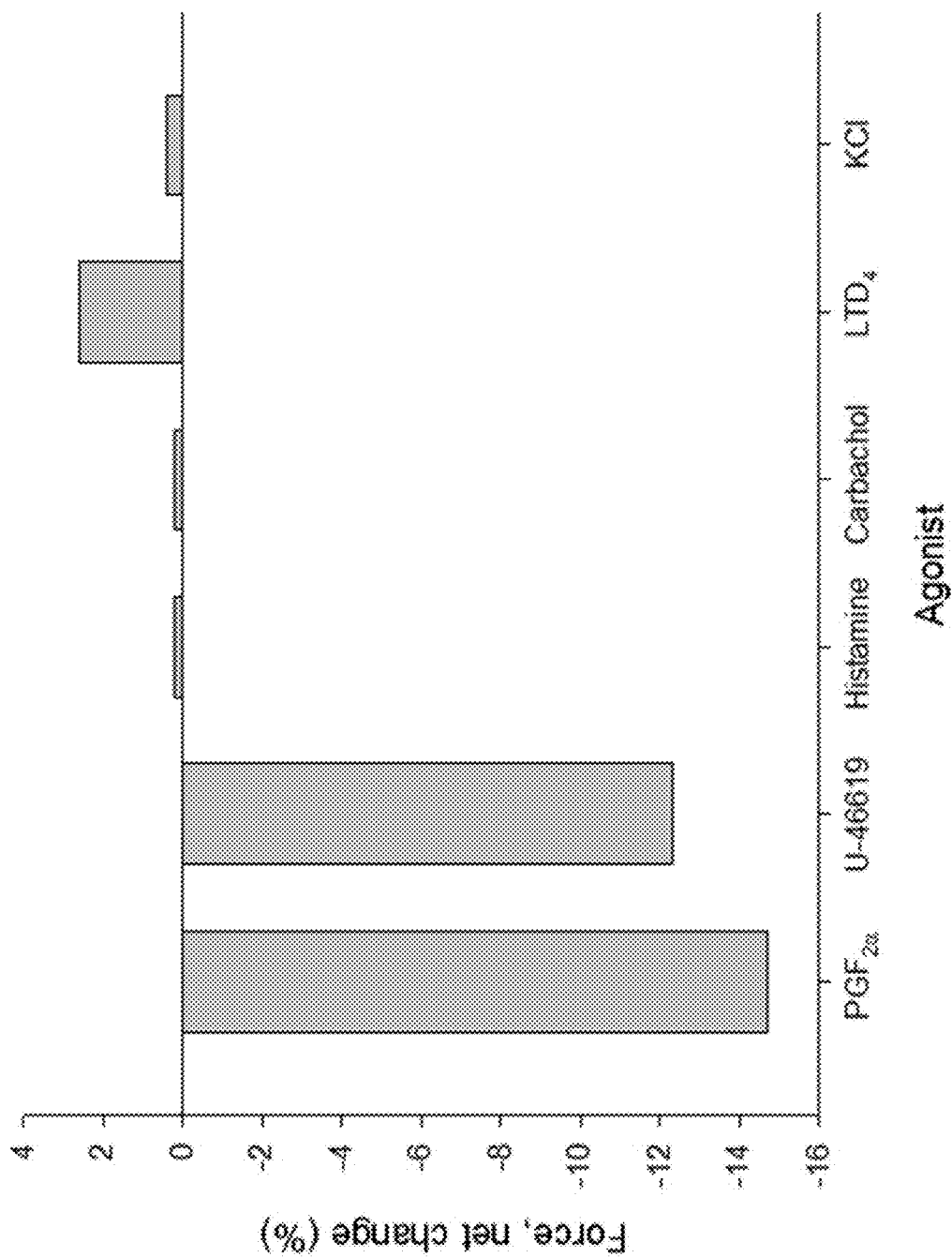
FIGS. 3 and 4 show the net change in bronchoconstriction (force) induced by PGF2α and other agonists after addition of pemirolast at concentrations of 10 and 110 μg/mL, respectively.

At 10 µg/mL, pemirolast also partially reversed the bronchoconstriction induced by 100 nM U-46619 (n=2), a selective TP receptor agonist (FIG. 3). Pemirolast at this concentration had no effect on the bronchoconstriction induced by histamine (1 µM, n=3), leukotriene $D_4$ (1 nM, n=3), carbachol (3 µM, n=4) or potassium chloride (KCl, 30 mM, n=2) (FIG. 3). The magnitude of the bronchoconstrictive responses to histamine, leukotriene $D_4$, carbachol and KCl was similar to that of $PGF_{2\alpha}$ (3 µM).

Figure 4:
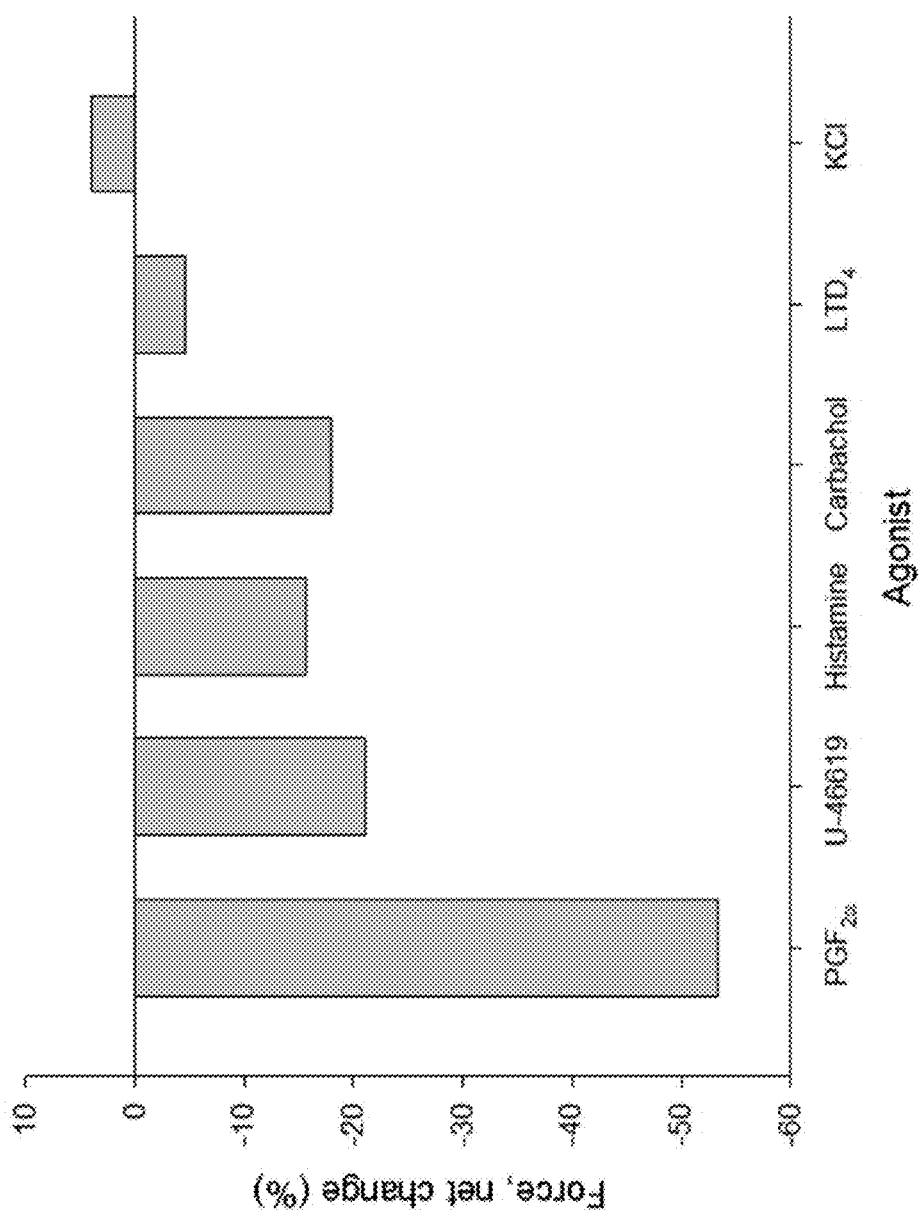

At 110 µg/mL, pemirolast caused a partial reversal of the bronchoconstriction induced by 100 nM U-46619, histamine (1 µM) and carbachol (3 µM), and had little effect on the responses to leukotriene $D_4$ (1 nM) and KCl (30 mM) (see FIG. 4, n=2-4 per agonist). The same experimental protocol as that used for $PGF_{2\alpha}$ was used for all the bronchoconstrictor agents.

Example 5

Clinical Trial

This study comprised male and female asthma patients (18 to 46 years of age) with a positive asthma test (as determined by a mannitol challenge test (vide infra) performed within 15 days prior to enrolment at the first screening visit, Visit 1).

At entry, about 20% of the patients had ongoing asthma treatment with long-acting beta2-agonists (LABA), and about 40% of the patients had ongoing asthma treatment with inhaled glucocorticosteroids (ICS).

It was a double-blind, randomized, placebo-controlled, cross-over trial assessing the efficacy of orally administered single doses of placebo and 40 mg and 400 mg of pemirolast (immediate release tablets containing pemirolast sodium hemihydrate, as well as microcrystalline cellulose, mannitol, copovidone fine, croscarmellose sodium, anhydrous colloidal silica and magnesium stearate) in patients challenged with mannitol inhalation as described below.

The patients were exposed to the different treatments at three separate hospital visits at least 2 (mean 6.8, median 6) days apart. The data reported in FIGS. 5 and 6 below represent the patients that received placebo treatment at the first visit (n=8) or placebo at the second visit (after 40 mg at the first visit (n=4) or after 400 mg at the first visit (n=4)).

All doses were administered 3 hours before initiation of the mannitol challenge test to ensure peak plasma concentrations of pemirolast when the mannitol challenge was performed (blood samples for analysing plasma concentrations of pemirolast were collected 3 hours after drug administration).

There were 5 visits during the trial: A screening visit (Visit 1, within 15 days before Visit 2), three visits for treatment with Investigational Medicinal Products (IMP; pemirolast 40 or 400 mg, or placebo) (Visit 2-4, spaced at least 2 days apart), and a final follow-up visit by telephone (Visit 5, at least 2, but less than 4 days after Visit 4 and within 30 days of Visit 2).

All laboratory pharmacokinetic analyses were performed by Clinical Pharmacology, Karolinska University Hospital, Stockholm, Sweden. Briefly, the concentration of pemirolast in human plasma was determined by solid phase extraction and liquid chromatography followed by tandem mass spectrometric detection (LC-MS/MS). The analytical method, utilizing a 200 µL sample aliquot, has a calibration range of 4.00-4000 ng/mL, with a lower limit of quantification (LLOQ) set at 4.00 ng/mL.

At Clinical Pharmacology the method has earlier been partially validated prior to sample analysis.

The trial was performed in compliance with Good Clinical Practice (GCP).

Inclusion Criteria were:
Written informed consent before the trial
Age ≥18 and <50 years Diagnosis of asthma according to Global Initiative for Asthma (GINA) Guidelines
Fractional exhaled nitric oxide (FENO) >20 ppb (calculated average of 2 independent FENO measurements)
Baseline FEV1>80% of the predicted normal value at Visit 1
Demonstration of PD15 at ≤315 mg mannitol
Exclusion Criteria were:
Lower respiratory tract infection <6 weeks prior to the trial
Influenza vaccination <4 weeks prior to the trial
Current smokers
Ex-smokers with a smoking history of >10 pack years (e.g. 10 pack years=1 pack/day×10 years, or ½ pack/day×20 years). An ex-smoker may be defined as a subject who has not smoked for >6 months prior to the trial
Treatment with any of the medications listed below <3 weeks prior to the trial:
  Inhaled steroids in a dose equivalent to >2×400 μg budesonide/day (dose must not be changed <4 weeks prior to and during the trial)
  Oral corticosteroids
  Any systemic immunomodulatory therapy
  Any systemic anti-rheumatic therapy
  Anti-IL-4 therapy
  Clinically significant comorbidities that may be compromised by induced bronchospasm or repeated spirometry as judged by Investigator
BMI>30
Known HIV positive
Known active hepatitis B or C
Significant concurrent, uncontrolled medical condition including, but not limited to, renal, hepatic, cardiac, haematological, gastrointestinal, endocrine, inflammatory, autoimmune, pulmonary, neurological, cerebral or psychiatric disease evaluated by the Investigator to interfere with effect of the trial drug
Subjects who have a clinically significant abnormal laboratory value and would be at potential risk if enrolled in the trial as evaluated by the Investigator
Known uncontrolled allergic conditions or allergy/hypersensitivity to any component of the trial drug or placebo excipients
Known uncontrolled allergic conditions or allergy/hypersensitivity to mannitol or gelatine used to make capsules
Breast-feeding female subjects
Female subjects of childbearing potential not willing to use adequate contraceptive methods (adequate contraceptive measures as required by local requirements or practice) during participation in the trial until at least 3 days after last intake of investigational drug
Male subjects not surgically sterilized, who or whose partner is not using adequate contraceptive methods (adequate contraceptive measures as required by local requirements or practice) during participation in the trial until at least 3 days after last intake of investigational drug
Receipt of any experimental agents within 30 days prior to the trial
Participation in any other interventional clinical trial during the trial period
Subjects known or suspected of not being able to comply with the trial protocol (e.g. due to alcoholism, drug dependency or psychological disorder)

The primary endpoint in the study was the Provocation Dose (PD) of mannitol resulting in a 15% fall in Forced Expiratory Volume during 1 second (FEV1; values given in Litres (L)) ($PD_{15}$ for mannitol), which is recognised by regulatory authorities as an acceptable method to evaluate potential efficacy of asthma drugs (*European Medicines Agency. Note for Guidance on Clinical Investigation of Medicinal Products for Treatment of Asthma*, 2013).

The mannitol challenge test (Aridol®, Pharmaxis Ltd, Frenchs Forest, Sydney Australia) was performed as follows: application of nose clip and challenge with 0 (empty capsule acting as placebo), 5, 10, 20, 40, 80, 160, 160, 160 and 160 mg of mannitol via the Halermatic (the 80 and 160 mg doses were given as multiple doses of 40 mg capsules). After inhalation, subjects were instructed to hold their breath for 5 seconds.

At least 2 repeatable FEV1 manoeuvres were performed 60 seconds after each dose and the highest FEV1 was used in the calculation. The FEV1 value taken after the 0 mg capsule was taken as pre-challenge FEV1 and used to calculate the percentage decrease in FEV1 in response to the mannitol challenge. The test was ended when the FEV1 had fallen by 15% or more. The mannitol PD15 in the trial participants days before the first drug treatment was 133 mg (Geometric mean, n=24).

A secondary endpoint in the study was to analyse changes in urinary excretion of a metabolite (11β-prostaglandin (PG) F2α) of the lung mast cell mediator/biomarker prostaglandin D2. 11β-PGF2α analysis was performed in unextracted urine samples using a validated enzyme immunoassays (EIA) kit from Cayman Chemical, Ann Arbor, Mich., USA (Item no 516521). Absolute values of the mediators were expressed as nanograms 11β-PGF2α per millimole creatinine.

At the days of treatment with IMP (pemirolast 40 or 400 mg, or placebo), and mannitol testing (Visit 2-4), the following procedure was followed:
1) Before IMP administration testing:
  a) Withdrawal from trial visit criteria to be checked
  b) Urine sampling for 11β-PGF2α analysis
  c) Blood sampling for haematology and blood biochemistry
  d) Vital signs, physical examination, adverse events and concomitant medication
2) Administration of IMP 3 hours (+/−10 min) before the mannitol challenge
3) Before mannitol challenge:
  a) <10 min before: Urine sampling for 11β-PGF2α analysis
  b) <10 min before: Blood sampling for analysis of plasma pemirolast concentration
4) Mannitol test 3 hours (+/−10 min) after IMP administration
5) After mannitol challenge:
  a) Urine sampling for 11β-PGF2α, 30 minutes after mannitol challenge
  b) Pregnancy test (Visit 4 only, in addition to prior to enrolment)
  e) Recording of concomitant medication just before sending the patient home
  f) Reporting of AEs just before sending the subject home The following treatments were not allowed from ≤3 weeks prior to the screening visit (Visit 1) and during the trial period:
  Inhaled steroids in a dose equivalent to >2×400 μg budesonide per day (dose must not be changed <6 weeks prior to Visit 1 and during the study)

Oral corticosteroids
Any systemic immunomodulatory therapy
Any systemic anti-rheumatic therapy
Anti-IL-4 therapy The following treatments were not allowed within the indicated time-frames:

| Time to withhold before mannitol challenge test was performed | Medication |
|---|---|
| 6-8 hours | Inhaled non-steroidal anti-inflammatory agents |
| 8 hours | Short acting Beta$_2$ agonists |
| 12 hours | Short-acting anticholinergic |
| 24 hours | Inhaled corticosteroids plus long-acting Beta$_2$ agonists |
| 24 hours | Long acting Beta$_2$ agonists |
| 72 hours | Antihistamines |
| 72 hours | Long-acting anticholinergic |
| 4 days | Leukotriene receptor antagonists |

Results

Long-Term Prophylaxis of Asthma

The results of the study showed that 3 hour pre-treatment with pemirolast increased the mannitol PD$_{15}$.

An unexpected and surprising finding in this study was that 400 mg, but not 40 mg, of pemirolast p.o. resulted in a prophylactic effect in relation to mannitol-induced asthma, which unexpectedly persisted beyond the elimination of pemirolast from circulation.

Figure 5:
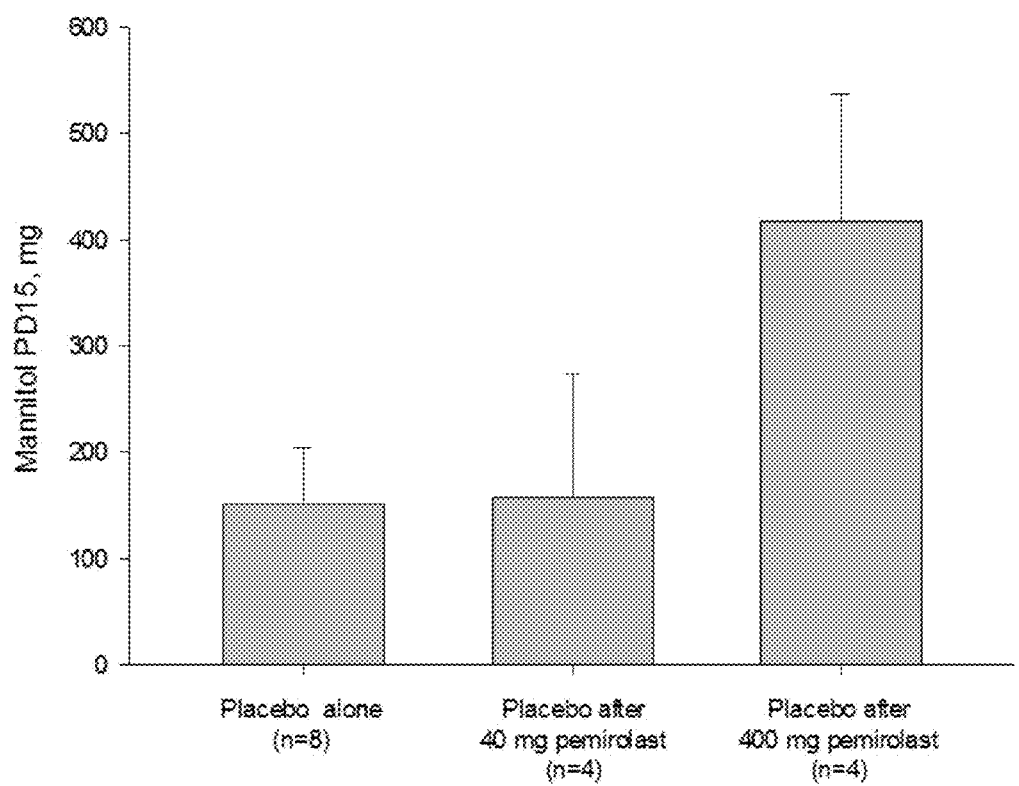
FIG. 5 shows back-transformed means and means+SEM for logged mannitol $PD_{15}$ for placebo treatments alone, preceded by a 40 mg dose of pemirolast, and preceded by a 400 mg dose of pemirolast.

As shown in FIG. 5, placebo-treated patients tolerated a much higher dose of mannitol when a single 400 mg dose of pemirolast was given at least 3 days before placebo/mannitol. This unexpected long-term prophylactic effect was not seen when the placebo treatment was preceded by a pemirolast dose of 40 mg.

The mean peak plasma concentrations of pemirolast 3 hours after the 40 and 400 mg doses have been found to be about 3,000 ng/mL and 35,000 ng/mL (with $t_{1/2}$ being about 4 to 7 hours), respectively (geometric mean values, n=23-24).

In all three experimental placebo groups presented in FIG. 5, the mean plasma concentrations of pemirolast were below the limit of quantification of the analytical method (4 ng/mL), and there were no relevant differences between the groups.

Treatment with 400 mg pemirolast for 3 hours did not per se increase FEV1 which was 3.58±0.86 L before treatment and 3.55±0.84 L 3 hours after an oral dose of 400 mg pemirolast (mean values±SD, n=22). This finding suggests that the lasting effect of pemirolast was not a result of a baseline bronchodilatory effect of pemirolast.

Furthermore, the long-lasting prophylactic effect resulting from the 400 mg dose of pemirolast did not seem related to inhibition of mast cells.

Prostaglandin D2 (PGD2) is released from mast cells (e.g. in the lung) and is known as a mediator of asthmatic bronchoconstriction (Hardy et al, *N. Engl. J. Med.*, 311, 209 (1984)). Urinary levels of the PGD2 metabolite 11β-PGF2α increase acutely during asthmatic attacks, including those induced by mannitol inhalation (Brannan et al, *Eur. Respir. J.*, 22, 491 (2003)). This PGD2 metabolite is therefore used as a biomarker for mast cell activation in asthmatics.

Figure 6:
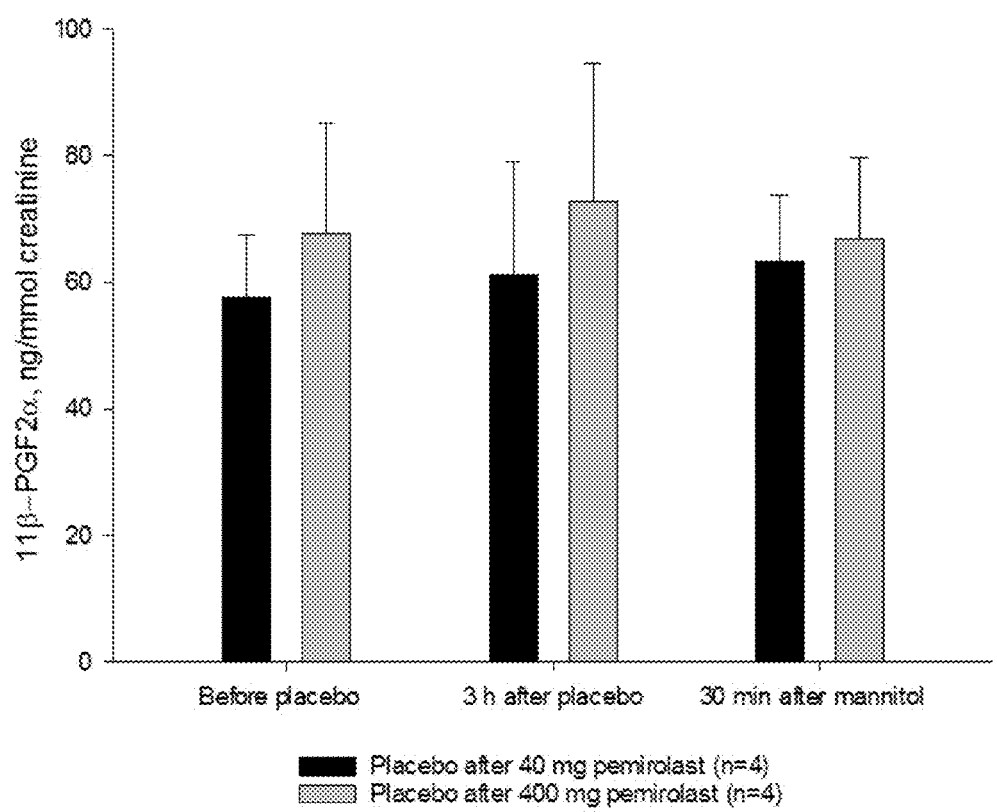
FIG. 6 shows levels of a PGD2 biomarker in urine as between patients treated (with reference to FIG. 5) with 40 mg and 400 mg.

Urinary levels of the PGD2 biomarker in urine did not differ between the patients that had previously (at least 3 days before) been treated with 40 mg or 400 mg (FIG. 6, same 4+4 patients as in FIG. 5). If anything, the levels of the mast cell biomarker tended to be slightly higher with the 400 mg dose than the 40 mg dose.

In this study, there were no serious adverse events or clinically significant changes in vital signs, findings at physical examination or in haematological or blood biochemistry laboratory tests.

Taken together, a dose of pemirolast higher than ever previously tested in asthmatics, causes an unexpected prophylactic anti-asthma effect that persists after the drug is cleared from the circulation and appears to be unrelated to inhibition of mast cells and direct bronchodilatory effects.

Mast Cell Silencing

Figure 7:
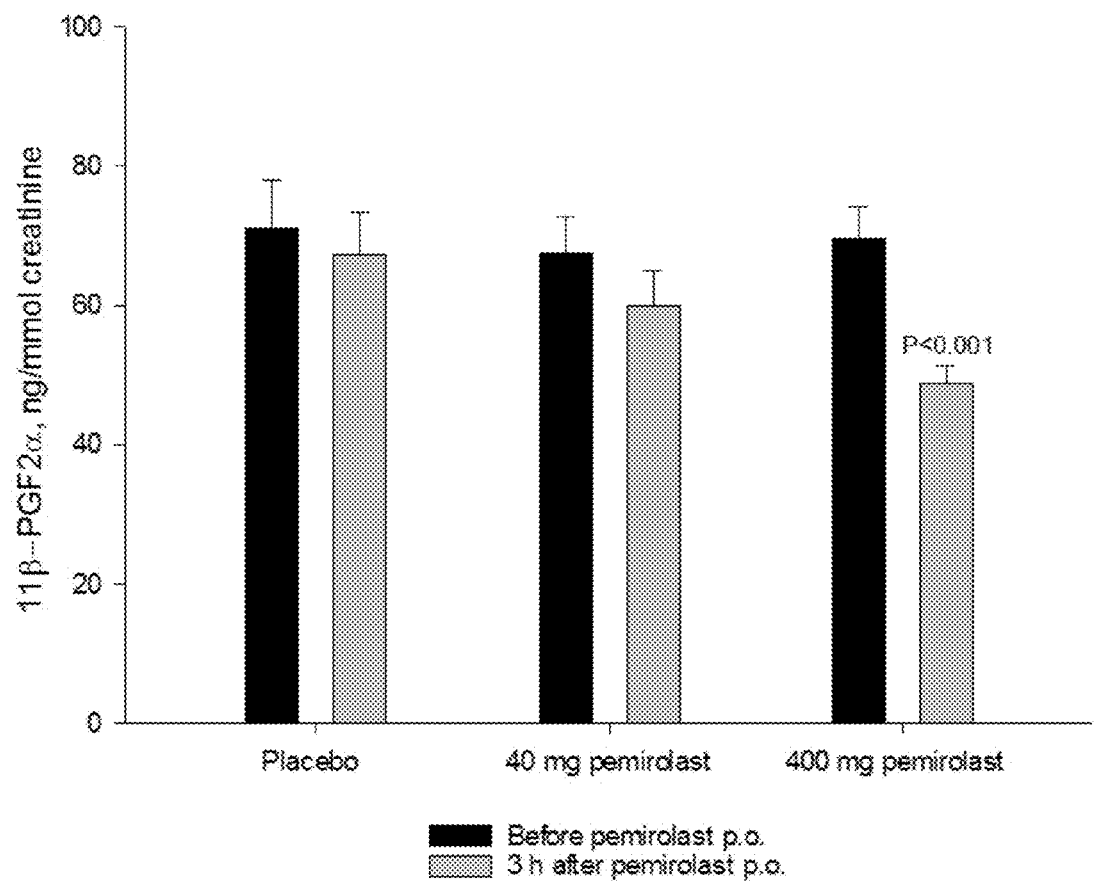
FIG. 7 shows baseline production of a PGD2 biomarker in asthmatics without ongoing attacks.

Measurement of PDG2 as described above also showed that, 3 hours after administration of 400 mg, but not 40 mg, doses of pemirolast, baseline production of PGD2 in asthmatics without ongoing attacks was significantly reduced (see FIG. 7; n=22-24).

This means that higher (than previously employed clinically) doses of pemirolast appear to significantly reduce baseline mast cell activity in asthmatics that are not experiencing ongoing attacks.

The invention claimed is:

1. A method for the treatment of asthma, which method comprises administering pemirolast, or a pharmaceutically acceptable salt thereof, to a human patient having asthma, wherein said administering is carried out by orally administering a dose effective to treat the asthma, which dose is at least about 300 mg per day (calculated as the free acid).

2. A method as claimed in claim 1 wherein the dose of pemirolast (calculated as the free acid) is at least about 350 mg per day.

3. A method as claimed in claim 1 wherein the dose of pemirolast (calculated as the free acid) is at least about 400 mg per day.

4. A method as claimed in claim 3 wherein the dose of pemirolast (calculated as the free acid) is up to about 600 mg per day.

5. A method as claimed in claim 1, wherein the daily dose of pemirolast or salt thereof is administered between once and four times daily in separate doses.

6. A method as claimed in claim 5, wherein the daily dose of pemirolast or salt thereof is administered twice daily in separate doses.

7. A method as claimed in claim 1, wherein the asthma is acute asthma.

8. A method as claimed in claim 1, wherein the asthma comprises an acute asthma attack.

* * * * *